United States Patent [19]
Herbert et al.

[11] Patent Number: 5,105,003
[45] Date of Patent: Apr. 14, 1992

[54] SEPARATION OF 1,2-DIHYDROXYCYCLOHEXA-3,5-DIENE COMPOUNDS

[75] Inventors: Andrew B. Herbert, Ontario, Canada; Gary N. Sheldrake, W. Yorks, England; Peter J. Somers, Birmingham, England; John A. Meredith, Gloucestershire, England

[73] Assignee: Imperial Chemical Industries PLC, London, England

[21] Appl. No.: 464,519

[22] Filed: Jan. 16, 1990

[30] Foreign Application Priority Data

Jan. 16, 1989 [GB] United Kingdom ................. 8900854

[51] Int. Cl.$^5$ ............................................... C07F 5/04
[52] U.S. Cl. .................................................... 558/288
[58] Field of Search ......................................... 558/288

[56] References Cited

U.S. PATENT DOCUMENTS 4,536,666  8/1985  Metz et al. ........................... 307/494
4,849,504  7/1989  Ballard et al. ...................... 528/491

FOREIGN PATENT DOCUMENTS 0076606  4/1983  European Pat. Off. ............ 558/288

Primary Examiner—Mary C. Lee
Assistant Examiner—Robert C. Whittenbaugh
Attorney, Agent, or Firm—Cushman, Darby & Cushman

[57] ABSTRACT

A process for the separation of a compound comprising a 1,2-dihydroxycyclohexa-3,5-diene ring from a medium containing it in which the compound reacts with a phenylboronate ion to form a phenylboronate ester which is insoluble in the medium. Novel phenylboronate esters formed during the separation process are also claimed.

7 Claims, No Drawings

SEPARATION OF 1,2-DIHYDROXYCYCLOHEXA-3,5-DIENE COMPOUNDS

This invention relates to a process for the separation of a compound comprising a 1,2-dihydroxycyclohexa-3,5-diene ring from a medium containing it, to a phenylboronate ester formed during the process and to a method for the production of the phenylboronate ester.

In our European Pat. No. 76606 we describe a process for the preparation of a compound comprising a 1,2-dihydroxycyclohexa-3,5-diene ring in which a mutant strain derived from a strain of *Pseudomonas putida* is first grown on a medium containing a suitable carbon source and then, after the growth period, is supplied with an aromatic compound in a medium which supports little or no growth of the mutant strain and the aromatic compound is converted into a compound comprising a 1,2-dihydroxycyclohexa-3,5-diene ring. Compounds which can be prepared by the process of European Patent No. 76606 include cis-1,2-dihydroxycyclohexa-3,5-diene, cis,1,2-dihydroxy-3-chlorocyclohexa-3,5-diene and cis-1,2-dihydroxy-3-methylcyclohexa-3,5-diene.

In our European Patent Application No. 250122 we describe a method for the preparation of cells of *Pseudomonas putida* suitable for use in the process of European Patent No. 76606 in which cells of a mutant strain of *Pseudomona putida* are grown in a culture medium containing an inducer compound (other than benzene or toluene) to induce in the cells an enzyme capable of converting an aromatic or substituted aromatic compound to a corresponding compound comprising a 1,2-dihydroxycyclohexa-3,5-diene ring. Preferred inducer compounds include pyridine and substituted pyridines.

A number of novel substituted cis-1,2-dihydroxycyclohexa-3,5-diene compounds, useful as intermediates in the production of phenols and catechols which are themselves useful as intermediates in the production of drugs, herbicides, insecticides and as chiral synthons, are described in our European Patent Application No. 253485.

Compounds comprising 1,2-dihydroxycyclohexa-3,5-diene rings generally have high solubilities in water and this causes separation problems during their production, e.g. in the process of European Patent No. 76606 and in the production of the novel compounds of European Patent Application No. 253485. In many instances known separation procedures cause other materials to be separated from reaction mixtures together with the produced 1,2-dihydroxycyclohexa-3,5-diene compounds. This makes it very difficult to obtain good extraction of these compounds with a high degree of purity.

According to the present invention we provide a process for the separation of a compound comprising a 1,2-dihydroxycyclohexa-3,5diene ring from a medium containing it which comprises the steps of (a) contacting the medium with a phenyl boronate ion having the structure

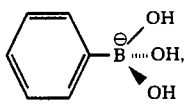

in which the phenyl group is substituted or unsubstituted, under conditions suitable for the formation of a complex between the compound and the ion; (b) adjusting the conditions to convert the complex into a neutral phenylboronate ester which is insoluble in the medium; and (c) separating the phenylboronate ester from the medium.

Further according to the present invention we provide a process for the separation and recovery of a compound comprising a 1,2-dihydroxycyclohexa-3,5diene ring from a medium containing it which comprises the steps of (a) contacting the medium with a phenyl boronate ion having the structure

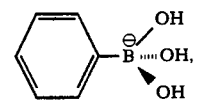

in which the phenyl group is substituted and unsubstituted, under conditions suitable for the formation of a complex between the compound and the ion; (b) adjusting the conditions to convert the complex into a neutral phenylboronate ester which is insoluble in the medium; (c) separating the phenylboronate ester from the medium; (d) subjecting the pheynlboronate ester to conditions which cause it to break into its component parts; and (d) separating the compound comprising a 1,2-dihydroxycyclohexa-3,5- diene ring from the ester components.

Further according to the present invention we provide phenylboronate esters having the general formula:

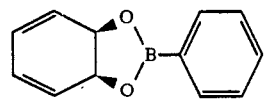

wherein the phenyl group and the cyclohexadienyl group are substituted or unsubstituted.

Further according to the present invention we provide a method for the preparation of a phenylboronate ester having the general formula:

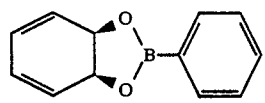

wherein the phenyl group and the cyclohexadienyl group are substituted or unsubstituted, which comprises the steps of (a) contacting a first compound comprising a 1,2-dihydroxycyclohexa-3,5-diene ring with a phenyl boronate ion having the structure

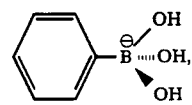

in which the phenyl group is substituted or unsubstituted, under conditions suitable for the formation of a complex between the first compound and the ion, (b) adjusting the conditions to convert the complex into a neutral phenylboronate ester which is insoluble in the medium; and (c) separating the phenylboronate ester thus formed from the reaction medium.

In the formulae shown above and elsewhere in this specification, the symbol ⊖ indicates a negative charge attached to a boron atom.

In the process of the invention the phenyl boronate ion used preferably has an unsubstituted phenyl group and is suitable formed by reaction 1:

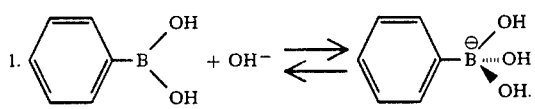

This reacts with the compound comprising a 1,2- dihydroxycyclohexa-3,5-diene ring, e.g. cis-1,2-dihydroxycyclohexa-3,5-diene according to reaction 2.

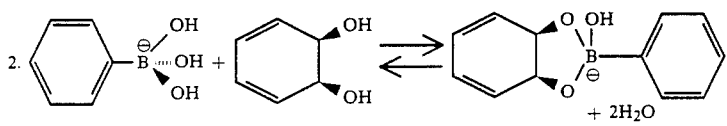

In step (b) of the process the conditions are changed causing the complex produced by reaction 2 to be converted by reaction 3 to a neutral phenylboronate ester:

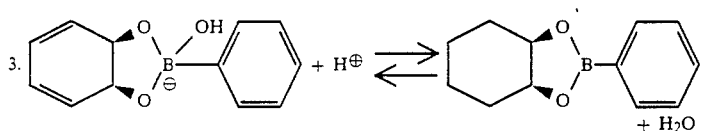

the unchanged neutral phenylboronate ester produced by reaction 3 is insoluble in water and enables the separation to be performed.

Suitably the process of the invention can be carried out using some or all of the following steps:

1. A first step in which an aqueous broth or centrifuged concentrate containing the compound comprising a 1,2-dihydroxycyclohexa-3,5-diene ring (the cyclodiene compound) is contacted with the phenyl boronate ion to produce a complex. This step is preferably performed at a pH in the range 10 to 13, a pH in the range 12 to 13 being particularly preferred.

2. A second step in which the pH is adjusted sufficient to cause the complex to be converted to the novel phenylboronate ester of the invention which separates as a solid complex from the solution. This step suitably can be performed immediately after the first step and in the same reaction vessel, e.g. by simple addition of acid to the reaction mixture of the first step. Preferably in the second step the pH is adjusted to a value in the range 7 to 7.5, pH 7 being particularly preferred. The phenylboronate ester may be separated as a third step from the liquid by filtration. The separated solid phenylboronate ester may itself form the product of the process or it may be further treated as described below to break it down and to form the cyclodiene compound.

3. A fourth step in which the solid phenylboronate ester separated in the third step is subjected to conditions sufficient to break it into a mixture of its component parts which can be separated.

Preferred compounds comprising a 1,2-dihydroxycyclohexa-3,4-diene ring which can be separated by the process of the invention include cis-1,2-dihydroxycyclohexa-3,5-diene; cis-1,2-dihydroxy-3-chlorocyclohexa-3,5-diene; cis-1,2-dihydroxy-3-methylcyclohexa-3,5-diene; cis-1,2-dihydroxy-3,6-difluorocyclohexa-3,5-diene; cis 1,2-dihydroxy-3-trifluoromethylcyclohexa-3,5-diene; and cis-1,2-dihydroxy-3-fluorocyclohexa-3,5-diene.

The process of the invention improves the separation of compounds comprising 1,2-dihydroxycyclohexa-3,5-diene rings from reaction mixtures containing them. It enables these compounds to be produced in better yields and with reduced levels of impurities.

The invention is illustrated by the following Examples:

EXAMPLE 1 cis-1,2-dihydroxy-3-methylcyclohexa-3,5-diene (hereinafter referred to as toluene-cis-glycol or TCG) was dissolved in deionised water to give a 5% (w/v) solution. Phenyl boric acid (48 g) was added to 1 litre TCG solution and solid sodium hydroxide was added until the solution reached pH 12.5. Concentrated hydrochloric acid was added until the mixture reached pH 7.4. The precipitated solid was filtered at the pump and dried in vacuo. The yield of precipitated solid was calculated by weight to be 95%. The physical properties of the product of this example were determined and its structure determined by IR and NMR measurements. The result is given as Compound No. 3 (toluene cis-glycol phenylboronate) in the Table following Example 2.

EXAMPLE 2

The process of Example 1 was repeated except that cis-1,2-dihydroxy-3-chlorocyclohexa-3,5-diene, cis-1,2-dihydroxy-3,6-difluorocyclohexa-3,5-diene, cis-1,2-dihydroxy-3-trifluoromethylcyclohexa-3,5-diene, and cis-1,2-dihydroxycyclohexa-3,5-diene were separately used instead of cis-1,2-dihydroxy-3-methylcyclohexa-3,5-diene. Precipitated solids were obtained in each case with yields of 90–95%.

The physical properties of the products were determined and their structures determined by IR and NMR measurements. The those from the differing compounds above being identified in the Table as follows:

Compound 4 - from cis-1,2-dihydroxy-3-chlorocyclohexa-3,5-diene

Compound 2 - from cis-1,2-dihydroxy-3-fluorocyclohexa-3,5-diene

Compound 6 - from cis-1,2-dihydroxy-3,6-difluorocyclohexa-3,5-diene

Compound 5 - from cis-1,2-dihydroxy-3-trifluoromethylcyclohexa-3,5-diene

Compound 1 - from cis-1,2-dihydroxycyclohexa-3,5-diene

Compound 3 - in the Table is the product of Example 1.

The basic structure of the compounds in the Table is as follows with the X and Y substitutents in compounds 1 to 6 being as indicated:

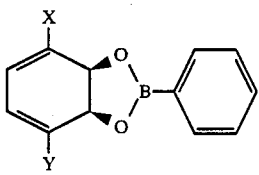

1. X = H,    Y = H       4. X = Cl,   Y = H
2. X = F,    Y = H       5. X = CF₃,  Y = H
3. X = CH₃   Y = H       6. X = F,    Y = F

TABLE

| Compound No. | δ ¹H ppm (CDCl₃, standard TMS) | δ ¹³C ppm (CDCl₃, standard TMS) | ≈ cm⁻¹ (KBr disc) | mpt. °C. |
| --- | --- | --- | --- | --- |
| 1. Benzene cis-glycol phenyl boronate | 5.16(S, 2H), 5.94 (S, 4H), 7.4(m, 3H) 7.8(m, 2H) | 71.8, 123.4, 124.4, 127.7, 131.3, 134.9 | 1200, 1050, 930 | 67 |
| 2. 3-Fluorobenzene cis-glycol phenylboronate | 5.13(m, 1H), 5.37 (m, 1H), 5.58(m, 1H), 15.72(m, 1H), 5.85 (m, 1H), 7.42(m, 3H), 7.85(m, 2H) | 71.4(d, J=24H₂), 75.4(d, J=6H₂) 101.8(d, J=18H₂) 121.0, 127.4, 131.3, 134.7, 157.6 (d, J=270H₂) | 1690, 1600 1440, 1190 | 69.5 |
| 3. Toluene cis-glycol phenylboronate | 1.90(S, 3H), 4.87 (m, 1H), 5.12(m, 1H) 5.62-5.82(m, 3H), 7.3-7.9(m, 5H) | 19.8, 73.1, 75.7 114.9, 119.2, 121,7, 124.2, 127.8, 131.4 135.0 | 2845, 1600, 1440 | 68.0 |
| 4. 3-Chlorobenzene cis-glyco. phenylboronate | 5.09(m, 1H), 5.31 (m, 1H), 5.88(m, 2H), 6.10(m, 1H), 7.3-7.9 (m, 5H) | 74.5, 75.7, 122.1, 122.3, 123.5, 127.7 131.6, 134.9 | 1655, 1600, 1440, 785 | 91.0 |
| 5. α, α, α, -Trifluorotoluene cis-glycol phenylboronate | 5.20(m, 1H), 5.29 (m, 1H), 5.97(m, 1H) 6.06(m, 1H), 6.50 (m, 1H), 7.4(m, 3H) 7.85(m, 2H) | 69.0, 73.0, 120.7 123.7, 124.5, 126.8, 127.9, 129.7, 131.8, 135.8 | 1600, 1440 1205 | 64.0 |
| 6. 3,6-Difluoro benzene cis-glycol phenyl boronate | 5.28(S, 2H), 5.45 (t, 2H, J=8H₂), 7.3-7.9(m, 5H) | 73.6, 99.8, 127.8, 131.9, 135.1, 154.2 (dd, J=269 and 7H₂) | 1700, 1600, 1440, 1180 | 112.5 |

EXAMPLE 3

This example illustrates formation of a precipitated product from a crude liquor produced by our process described in European Patent No. 0076606.

A product liquor containing cis-1,2-dihydroxy-3-fluorocyclohexa-3,5-diene (fluorobenzne-cis-glycol or FBCG) was made by contacting fluorobenzene with mutant bacterial cells as in our process described in European Patent No. 0076606. The cells were removed from the product liquor by centrifugation and the supernatent concentrated by evaporation at 60° C. under vacuum giving a concentrated liquor containing FBCG at 12.6% (*/v). Filter aid (40 g "CLARCEL FLO 1"- British Ceca, Wimbledon, London) was charged with stirring to 400 g concentrated FBCG liquor. The mixture was filtered by suction with a Buchner funnel and flask and the solid was washed with water (20 g). Phenyl boric acid (48 g) was charged with stirring to the filtrate and solid sodium hydroxide was added until the solution reached pH 12.5. Concentrated hydrochloric acid was added until the mixture reached pH 7.4. The precipitated solid solid was 79 g (94%). The crude solid was recrystallised from ethanol to give white needles (53.2 g. 64%).

EXAMPLE 4

FBCG liquor was made in our process described in European Patent No. 0076606 and concentrated FBCG liquor prepared as described in Example 3. Concentrated liquor was filtered through an ultrafiltration membrane (Amicon Ltd., 100,000 nominal molecular weight cut off) in a DC10 module at an average flux of 15 l/m²/hr.

The ultrafiltered liquor was charged with phenyl boric acid with stirring and solid sodium hydroxide added until the solution reached pH 12.5. Concentrated hydrochloric acid was added until the mixture reached pH 7.4. The precipitated solid was filtered at the pump and dried in vacuo. The yield on FBCG in the solid was 96%.

We claim:

1. A process for the separation of a compound comprising a 1,2-dihydroxycyclohexa-3,5-diene ring as a phenylboronate ester derived therefrom from a medium containing it which comprises the steps of (a) contacting the medium with a phenylboronate ion having the structure

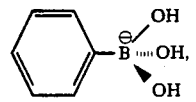

in which the phenyl group is substituted or unsubstituted, under conditions suitable for the formation of a complex between the compound and the ion of formula

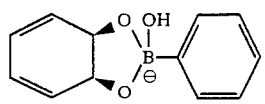

(b) adjusting the conditions to convert the complex into a neutral phenylboronate ester which is insoluble in the medium of formula

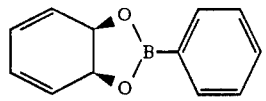

and (c) separating the phenylboronate ester from the medium.

2. A process for the separation and recovery of a compound comprising a 1,2-dihydroxycyclohexa-3,5-diene ring from a medium containing it which comprises the steps of (a) contacting the medium with a phenylboronate ion having the structure

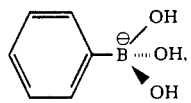

in which the phenyl group is substituted or unsubstituted, under conditions suitable for the formation of a complex between the compound and the ion of formula

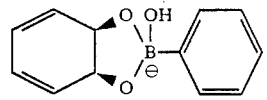

(b) adjusting the conditions to convert the complex into a neutral phenylboronate ester which is insoluble in the medium of formula (c) separating the phenylboronate ester from the medium; (d) subjecting the phenylboronate ester to conditions which cause it to break into its component parts; and (e) separating the compound comprising a 1,2-dihydroxycyclohexa-3,5-diene from the the ester components.

3. A process according to claim 1 wherein the phenylboronate ion has an unsubstituted phenyl group.

4. A process according to claim 1 wherein step (a) is performed at a pH in the range 10 to 13.

5. A process according to claim 4 wherein step (a) is performed at a pH in the range 12 to 13.

6. A process according to claim 1 wherein step (a) is performed at a pH in the range 7 to 7.5.

7. A process according to claim 1 wherein the compound comprising a 1,2-dihydroxycyclohexa-3,5-diene ring is cis-1,2-dihydroxycyclohexa-3,4-diene; cis-1,2-dihydroxy-3-chloro-cyclohexa-3,5-diene; cis-1,2-dihydroxy-3-methyl-cyclohexa-3,5-diene; cis-1,2-dihydroxyl-3,6-difluorocyclohexa-3,5-diene; cis-1,2-dihydroxy-3-trifluoromethylcyclohexa-3,5-diene; or cis-1,2-dihydroxy-3-fluorocyclohexa-3,5-diene.

* * * * *